(12) United States Patent
Boday et al.

(10) Patent No.: US 10,010,627 B2
(45) Date of Patent: Jul. 3, 2018

(54) MODIFIED POLYCATIONIC POLYMERS

(71) Applicant: International Business Machines Corporation, Armonk, NY (US)

(72) Inventors: Dylan J. Boday, Austin, TX (US); Jeannette M. Garcia, San Leandro, CA (US); James L. Hedrick, Pleasanton, CA (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/173,313

(22) Filed: Jun. 3, 2016

(65) Prior Publication Data

US 2017/0348432 A1    Dec. 7, 2017

(51) Int. Cl.
*A61K 48/00* (2006.01)
*C08G 73/02* (2006.01)
*C12N 15/113* (2010.01)

(52) U.S. Cl.
CPC ...... *A61K 48/0041* (2013.01); *C08G 73/0206* (2013.01); *C08G 73/0213* (2013.01)

(58) Field of Classification Search
None
See application file for complete search history.

(56) References Cited

U.S. PATENT DOCUMENTS

| | | | |
|---|---|---|---|
| 6,013,240 A | 1/2000 | Behr et al. | |
| 6,309,660 B1 | 10/2001 | Hsu et al. | |
| 8,535,586 B2 | 9/2013 | Yan et al. | |
| 8,623,325 B2 | 1/2014 | Robillard et al. | |
| 8,936,907 B2 | 1/2015 | Guire et al. | |
| 2014/0271814 A1* | 9/2014 | Andrali | A61K 9/1271 424/450 |

FOREIGN PATENT DOCUMENTS

| | | |
|---|---|---|
| CA | 2717788 A1 | 1/2009 |
| WO | 2013036082 A2 | 3/2013 |

OTHER PUBLICATIONS http://www.who.int/genomics/public/geneticdiseases/en/index2.html, published by the World Health Organization, 2005, Washington, DC, no author listed, pp. 1-10 printed.*
https://en.wikipedia.org/w/index.php?title=Special:ElectronPdf&page=Genetic+disorder&action=show-selection-screen&coll-download-url=%2Fw%2Findex.php%3Ftitle%3DSpecial%3ABook%26bookcmd%3Drender_article%26arttitle%3DGenetic%2Bdisorder%26returnto%3DGenetic%2Bdisorder%26oldid%3D784845115%26writer%3Drdf2latex, Wikipedia, San Francisco, CA, no author.*
http://learn.genetics.utah.edu/content/genetherapy/challenges/, author unknown, 2010, "Challenges in Gene therapy", published by the University of Utah, 4 pages printed.*
Matsumori, et al. (2011) "Design and Synthesis of Sphingomyelin-Cholesterol Conjugates and Their Formation of Ordered Membranes", Chemistry A European Journal, 17: 8568-75.*

* cited by examiner

*Primary Examiner* — Robert M Kelly
(74) *Attorney, Agent, or Firm* — Patterson + Sheridan, LLP (57) ABSTRACT

A polymeric material comprising a polyethylenimine-based material including the following moiety:

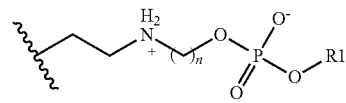

attached thereto, wherein R1 is a group including at least one carbon atom and n is from 2 to 4 is disclosed. A method for preparing a polyethylenimine-based material is disclosed. A gene therapy method using a polymeric material including polyethylenimine-based material is also disclosed.

20 Claims, 3 Drawing Sheets

MODIFIED POLYCATIONIC POLYMERS

BACKGROUND

The present disclosure relates to modified polycationic polymeric materials and methods of modifying polycationic polymeric materials such as modified polyethylenimines having possible uses in gene or drug delivery, flocculating agents, or membranes, amongst others.

Polyethylenimines (also sometimes referred to as poly (ethylenimine), poly(iminoethylene), polyaziridine, and poly[imino(1,2-ethanediyl)]) are polycationic polymeric materials which, among many other uses, have been investigated as transfection agents in gene therapy applications. That is, polyethylenimines have been investigated as a possible delivery vehicle for genetic material payloads (e.g., DNA and RNA) to be incorporated (transfected) into targeted cells for therapeutic purposes. Other possible uses of polyethylenimines are found in detergents, adhesives, water treatment, and paper making.

Polycationic polymers in general, and polyethylenimines in particular, have been widely studied as polymeric gene delivery vehicles for use in gene therapy applications. That is, these polycationic materials have been investigated as means for protecting genetic material payloads (e.g., DNA and RNA) from enzymatic degradation and the like during transport through the body to targeted cells or tissue. Polyethylenimines are known to form polyplexes or polycondensates with genetic material due to electrostatic interactions between the amine groups of the polyethylenimine and phosphate groups in the nucleic acids making up the genetic material. Furthermore, materials with a polycationic character are considered to promote intake of the genetic material payload by target cells by promoting binding of polyplexes to the generally negatively charged cellular membrane. Once bound to the cellular membrane, the polyplex can pass into the interior of the cell by endocytosis. Once inside the cell, it still remains necessary for the genetic material to be released from the endosome into the cytoplasm and then reach the transcription mechanism inside the cell nucleus. Polyethylenimines provide a mechanism (the "proton sponge effect") for rupturing the endosome and releasing the polyplex into the cytoplasm. Likewise the electrostatic nature of the binding between the polyethylenimine and the genetic material provides a means for releasing the genetic material into the cytoplasm for eventual diffusion into the nucleus. However, polyethylenimines are, in general, considered highly cytotoxic and, depending on molecular weight, may also be bioaccumulative. Since typical polyethylenimines are not readily biodegradable, in vivo accumulation is potentially problematic, especially given the known cytotoxicity.

Furthermore, polyethylenimines, and polycationic gene delivery vehicles more broadly, are known to cause problems when the overall positive charging of the polyplex relative to complexed genetic material is increased. In general, polycationic-genetic material complexes are more easily incorporated into cellular targets than bare genetic material because the polycationic material shields/mitigates the inherent negative charges of the genetic material, which would otherwise cause the genetic material to be repulsed by the cellular membrane. The binding of the polyplex to the cellular membrane is generally improved with increased positive charge, and thus ultimately uptake of the polyplex by a target cell is improved by increasing positive charging of the polyplex. However, polyplexes with substantial overall positive charge may themselves require shielding while within the various transport pathways of the body. For example, without shielding the polyplexes may trigger unintended immune system responses and interactions with blood components (e.g., plasma proteins), which might cause premature removal of the polyplex and/or dangerous aggregation of components within the blood stream or tissue. In some instances, a polyplex core of a delivery vehicle may in turn be shielded using materials like polyethylene glycol (PEG) or polyacrylic acid. However, providing additional shielding for the polyplex in this manner will tend to reduce effectiveness with respect to target cell binding and the genetic payload's bioavailability once inside the target cell. As such, existing polymeric gene therapy delivery vehicles face issues regarding cytotoxicity, transfection efficiency, bioaccumulation, and/or unintended interactions during transport to cellular targets. Therefore, development of improved materials for polymeric gene delivery vehicles for gene therapy applications is desirable.

SUMMARY

According to one embodiment, a polymeric material comprising a polyethylenimine-based component including a group:

wherein R1 includes a carbon atom and n is from 2 to 4. The group is attached to the polyethylenimine-based component at the end (wavy line) opposite the R1 end. In some embodiments, R1 can be an alkyl group, an aryl group, a polymeric group, an oligomeric group, a linkage to a polymeric group, or a linkage to an oligomeric group.

According to another embodiment, a method of making a polymeric material includes contacting a polyethylenimine-based material corresponding to the following:

and a cyclic phosphotriester corresponding to the following:

wherein R1 includes a carbon atom, n is from 2 to 4, each instance of R2 is independently one of a hydrogen atom, a linear polyethylenimine segment, or a branched polyethylenimine segment, and m is such that a weight-average molecular weight (Mw) of the polyethylenimine-based material is between 100 Da to $10^7$ Da. In some embodiments, R1 can be an alkyl group, an aryl group, a polymeric group, an oligomeric group, a linkage to a polymeric group, or a linkage to an oligomeric group According to another embodiment, a method comprises complexing a genetic material and a polymeric material including a polyethylenimine-based component including having a group corresponding to the following:

wherein R1 includes a carbon atom, and n is from 2 to 4. In some embodiments, R1 can be an alkyl group, an aryl group, a polymeric group, an oligomeric group, a linkage to a polymeric group, or a linkage to an oligomeric group.

DETAILED DESCRIPTION

A polymeric material can be prepared by reacting a cyclic phosphotriester ("CPTE") with a polyethylenimine ("PEI") material in a single-step, catalyst-free nucleophilic addition reaction with pendant primary amines of the PEI, according to the following scheme:

In scheme (I), n can be from 2 to 4, R1 includes at least one carbon atom, and the PEI material can be linear or branched. In this context, "branched" includes any PEI material with at least one tertiary amine unit in the polymeric chain. Furthermore, "branched" in this context includes so-called "dendrimeric" and "hyperbranched" PEI materials. In general, R1 can be alkyl, aryl, polymeric, or oligomeric. Also, the PEI material may itself be linked to with other polymeric components. For example, in addition to being a homopolymer of PEI repeat units, the PEI material may be copolymerized with other polymeric components or other polymeric materials may be grafted on to the PEI material. In such cases, the depicted "PEI" group in scheme (I) material may be referred to a PEI-based component. The terms defined above apply in the same way to PEI-based components.

A mixture of different CPTE types (e.g., different R1 groups) may be used in scheme (I). Likewise, the PEI material may be a mixture of different materials (e.g., different molecular weights or branching morphologies). As noted, the PEI material may also be copolymeric materials in which PEI repeating unit segments are interspersed with or connected to other repeating unit types, for example, and without limitation, polyethylene segments. The PEI materials may also include additional pendant and/or end groups other than primary amine groups, though at least one primary amine group must be present in the PEI-based reactant material.

The modified PEI material resulting from scheme (I) includes a zwitterionic moiety, which provides both positive and negative charges within the same molecule. Zwitterions are sometimes referred to as dipolar ions or intermolecular salts. In general, the number of zwitterionic moieties incorporated into the modified PEI will depend on reaction conditions and amount of CPTE in the reaction mixture as compared to the number of available amino end groups in the PEI material.

The zwitterionic moiety imparts a higher hydrophilicity to the resulting modified PEI material. As such, when the modified polymer (i.e. the material resulting from scheme (I)) is placed in an aqueous media, it possible for a hydration layer to form around the polymer. The formation of a hydration layer is considered one of the key requisites for imparting so-called "stealth" properties to biomaterials. For example, polyethylene glycol (PEG) materials, which are thought to form a hydration layer when in aqueous media, are well known "stealth" materials that are often adopted in biological applications. In this context, "stealth" refers to the ability of the materials to resist cell adhesion, antibody opsonization, and non-specific protein interactions. Materials with these "stealth" properties are less likely to be detected and cleared by immune system and/or form dangerous aggregations due to interaction with blood plasma proteins or the like.

Additionally, zwitterionic polymers are considered to be potentially biomimetic since they share structural similarities with the phosphatidylcholine-based moieties of biological membranes.

The reaction (see scheme (I)) between PEI-based materials and CPTE can be performed without catalysis and, in general, proceeds at room temperature. The reaction can be carried out in solvents which dissolve the PEI-based material. Polyethylenimines are typically soluble in polar solvents such as water, methanol, or acetonitrile depending on the particulars of structure such as degree of polymerization and branching. For example, branched polyethylenimines can be soluble in water, while linear polyethylenimines may require a stronger solvent (such as acetonitrile) to be solubilized.

Additionally, while the reaction between PEI-based materials and CPTE is promoted when the reactants are solubilized, reaction may still occur even when solid PEI-based material is exposed to the CPTE. However, the extent of reaction in a bulk phase process might be limited by the inaccessibility of amino end groups in a solid PEI-based material, which would result in few if any interactions with reactable CPTE molecules. Since the reaction between CPTE and primary amine groups of the PEI-based material proceeds via a ring opening mechanism, the relaxation of ring strain is considered the impetus for the reaction. As such the maximum number of atoms in CPTE ring is limited by the necessity of providing sufficient strain to make opening the ring energetically favorable. A 5 to 7 atom ring for the CPTE molecule is considered generally suitable in this regard.

Figure 1:
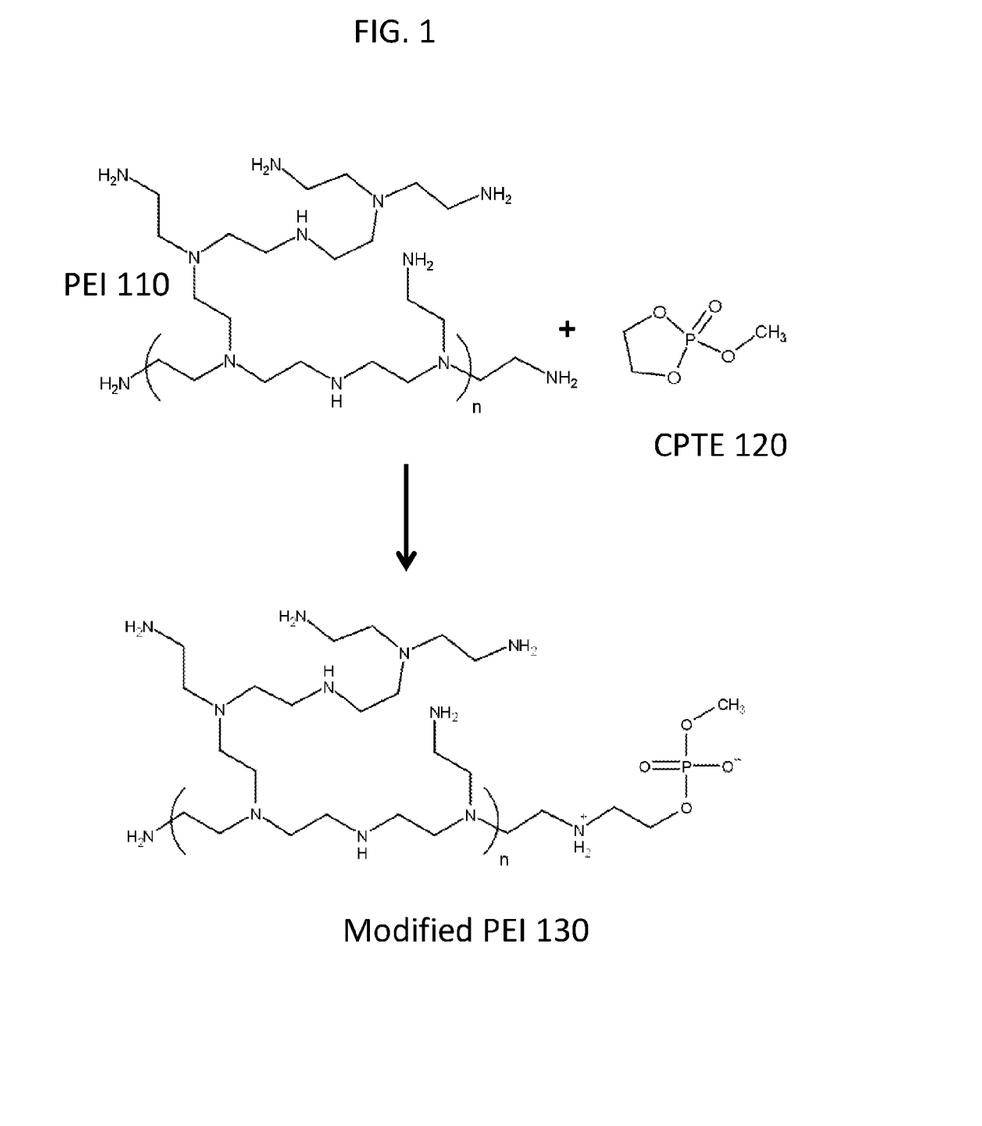
FIG. 1 depicts an example reaction for forming a modified polycationic polymeric material according to an embodiment.

FIG. 1 depicts an example reaction between a PEI 110 and a CPTE 120 to form a modified PEI 130. The depicted PEI

110 is a branched PEI, but as discussed further below, this is merely to one possible structural example of a PEI-based material and other variants are possible such as linear and dendrimeric materials. The particularly depicted CPTE 120 material may be referred to as 2-methoxy-1,3,2λ5-dioxaphospholan-2-one As discussed further below, the depicted CPTE 120 is one possible structural example of a CPTE and other variants are possible. Furthermore, while the modified PEI 130 is depicted with unreacted primary amino end groups, the modified PEI 130 may also have two or more reacted primary amine groups and, furthermore, all or substantially all primary amine end groups may be reacted with the CPTE 120 in some embodiments.

CPTE Materials

In general, CPTE materials can be ring-opened to form poly(phosphotriesters) with an alcoholic initiator in the presence of the appropriate catalyst. The resulting materials are generally considered biocompatible and biodegradable and have themselves been investigated as delivery agents for therapeutics.

A variety of cyclic phosphotriesters are commercially available. Synthesis of various cyclic phosphotriesters can be conducted in one step and functionality can be readily introduced to these materials. For example, the specifically depicted CPTE 120 in FIG. 1 can be prepared by reaction of methanol with 2-chloro-2-oxo-1,3,2-dioxaphospholane.

As disclosed in scheme (I) above (and depicted in FIG. 1), various CPTEs can be used to modify polyethylenimines and polyethylenimine-based materials in a single step via a catalyst-free nucleophilic addition reaction with at least one primary amine of the polyethylenimine and polyethylenimine-based material being modified.

In general, a CPTE 120 molecule corresponds to the following:

where n=2, 3, or 4, and R1 includes at least one carbon. In various examples, R1 can include an alkyl group, an aryl group, a polymeric group, an oligomeric group, and/or a functional group permitting linkage to an alkyl group, an aryl group, a polymeric group, or an oligomeric group. In any specific reaction mixture, a mixture of different CPTE 120 molecules may be present.

Some possible structural examples of CPTE 120 are, without limitation:

where R1 includes at least one carbon;

where R1 includes at least one carbon;

where R1 includes at least one carbon;

where n is zero or greater.

In each of the above examples having an R1 group, R1 can include, without limitation, an alkyl group, an aryl group, a polymeric group, an oligomeric group, or a functional group permitting subsequent linkage to an alkyl group, aryl group, a polymeric group, or an oligomeric group.

PEI Materials

Polyethylenimines can be obtained commercially, or by direct synthesis, in a variety of forms such as linear, branched, and dendrimeric. Several methods are known for preparation of polyethylenimines such as the ring opening polymerization of aziridine and the hydrolysis of poly(2-ethyl-2-oxazoline).

In general, a PEI 110 has a structure corresponding to the following:

(II)

where each instance of R2 in material (II) is independently one of a hydrogen atom, a linear polyethylenimine segment, or a branched polyethylenimine segment, and m is such that a weight-average molecular weight (Mw) of the PEI 110 material is between 100 Da to $10^7$ Da.

Linear PEIs have the following general structure:

(III)

where n is an integer and variable dependent on intended end use. For example, n in material (III) may be greater than 2 up to tens of thousands for any specific polymer molecule. The weight-average molecular weight (Mw) for a linear PEI material would be in range of about 100 Da to $10^7$ Da. Typically, for gene therapy applications, the average molecular weight of a polymeric gene delivery vehicle is in a range of 10 kDa to 50 kDa.

Branched PEIs include a mixture of repeating units having secondary and tertiary amine groups. That is, any given repeat unit in the polymer may be one of:

(secondary amine repeat unit) and (tertiary amine repeat unit)

where attachment between repeat units is made ethyl-end to nitrogen-end. In the above, n and m designate that the depicted groups are repeating units within a branched PEI material and correspond to statistical relative ratios (compositional percentages) within a given branched PEI 110 material. A linear polyethylenimine segment corresponds to two or more secondary amine repeating groups directly connected to each other. A branched polyethylenimine segment includes a tertiary amine group connected to two other repeat units, either of which or both can be a secondary amine group or a tertiary amine group. The ratio of secondary to tertiary repeating units is not limited and, as noted above, all or substantially all repeating units may be secondary amine groups (in which case the PEI 110 would be linear or substantially linear). In cases where all or substantially all of the repeating units are tertiary amine groups, PEI 110 would be considered dendrimeric or hyperbranched material. The specific morphology of the branched PEI material is not limited and, as such, the branching and linear segments can be essentially randomly distributed within the PEI 110 material or the connective ordering may be controlled in some manner—for example, each tertiary amine group might be connected to at least one secondary amine group before another tertiary amine group is connected to the chain. The weight-average molecular weight (Mw) of a branched PEI 110 would be in a range of 100 Da to $10^7$ and when intended for gene therapy application more typically in the 10 kDa to 50 kDa range. An existing branched PEI material having a 25 kDa molecular weight is considered to have particularly good gene transfection efficiency for in vitro applications.

A strictly linear PEI 110 material would have only two primary amine end group which could react with the CPTE 120. Thus, such a modified linear PEI 130 would incorporate at best only two zwitterionic moieties, which depending on expected end use might or might not be sufficient. A branched PEI 110 material might be preferable for producing materials for applications in which a greater number of zwitterionic moieties would be advantageous and/or applications requiring primary amine groups and more than two zwitterionic moieties. The extent of branching can be varied by selection of synthetic methods and reaction conditions used to form the PEI 110 material. The branching in a PEI 110 material can be relatively minor or substantial. Linear, branched, hyperbranched, and dendrimeric forms of PEI are available commercially and/or available by known synthetic routes.

Some possible structural examples of PEI 110 are, without limitation:

(a linear PEI)

where n is 1 or more;

(a branched PEI)

where n is 1 or more, and;

(a dendrimeric PEI)

The example dendrimeric PEI above is a fourth generation dendrimer, but the number of generations is not limited and may be greater or less than four. With respect to branched polyethylenimines, those skilled in the art will recognize from the depicted example and above explanation that a great variety of possible structures are possible for a branched PEI 110. Furthermore, a branched PEI 110 could consist of a substantially random assortment of branching segments and linear segments or the arrangement of branching and linear segments could be ordered in some particular manner, such as specific length linear segments between branching segments

The PEI 110 material is furthermore not limited to homopolymers of polyethylenimine, but may be a copolymeric material including, for example, polyethylene, polyethylene glycol, polycarbonate, and/or biodegradable polymeric repeat units, either randomly distributed when synthetically possible or in distinct blocks. Possible biodegradable polymeric segments include poly(acrylamide), poly(vinyl pyrrolidone), and poly(glycerol) segments or corresponding repeat units. The polymeric materials of various compositions may likewise be grafted to the polyethylenimine-based components before or after modification with CPTE.

Modified PEI Material

The modified PEI-based material produced according scheme (I) corresponds to a material including at least one group corresponding to the following:

(IV)

wherein the above group (IV) is attached to a polyethylenimine-based material at the "starred" bond, R1 is includes at least one carbon atom, and n is from 2 to 4. In this context, a "polyethylenimine-based material" or a "polyethylenimine-based component" includes a linear or branched material including repeating units comprising at least one of the following:

(V)
and
(VI)

In the above structures (V) and (VI), n and m designate that the depicted groups are repeating units within a polyethylenimine-based material and correspond to statistical relative ratios (compositional percentages) within a given polyethylenimine-based material when given numerical values. For a linear or substantially linear polyethylenimine-based material, the ratio of m to n would be zero or approximately zero. For a dendrimeric polyethylenimine-based material, the ratio of n to m could be zero or approximately zero. The starred bonds on the amine ends of structures (V) and (VI) correspond to attachment points to the group (IV), a primary amine end group (*—CH$_2$—CH$_2$—NH$_3$), an ethyl end of another repeating unit (V)/(VI), or a connection point to other copolymer repeat units. The starred bonds on the ethyl ends of structures (V) and (VI) correspond to attachment points to the amine end of another repeating unit (V)/(VI), a primary amine end group (*—NH$_3$), a connection point to other copolymer repeat units, or a group corresponding to (IV) without an ethyl spacer group between the nitrogen atom in (IV) and the connection points. In some embodiments, R1 can be an alkyl group, an aryl group, a polymeric group, an oligomeric group, a linkage to a polymeric group, or a linkage to an oligomeric group. For example, R1 can be a methyl, ethyl, propyl, or higher alkyl group. Here, a polymeric or oligomeric group incorporated in to R1 may be, without limitation, a polyethylene material, a polyethylene glycol material, or derivatives of the materials.

A modified PEI 130 as depicted in FIG. 1, includes at least one group (IV) appended to a polyethylenimine-based material. The number of groups (IV) is not limited to one. In some embodiments, all or substantially all end groups of a modified PEI 130 material may be represented as either of the following:

(VII)
or (VIII)

wherein connection to a polyethylenimine-based material is implicit in (VII) and the "PEI" of (VIII) is taken to correspond to a polyethylenimine-based material as described above. In (VII) and (VIII), n is 2 to 4, and R1 includes at least one carbon atom. In some embodiments, R1 can be an alkyl group, an aryl group, a polymeric group, an oligomeric group, a linkage to a polymeric group, or a linkage to an oligomeric group.

Some possible structural examples of a modified PEI 130 are, without limitation:

where n is within a range providing the modified PEI-based material with a weight-average molecular weight (Mw) of 100 Da to $10^7$ Da, R1 includes at least one carbon atom;

where n is within a range providing the modified PEI molecules with a molecular weight of 100 Da to $10^7$ Da;

where n is 2 to 4, R1 includes at least one carbon atom, R2 is independently one of a hydrogen atom, a linear polyethylenimine segment, or a branched polyethylenimine segment, and m is such that a weight-average molecular weight (Mw) of the modified PEI material is between 100 Da to $10^7$ Da;

where n is 2 to 4, p is 2 to 4, R1 includes at least one carbon atom, R3 includes at least one carbon atom, R2 is independently one of a hydrogen atom, a linear polyethylenimine segment, or a branched polyethylenimine segment, and m is such that a weight-average molecular weight (Mw) of the modified PEI is between 100 Da to $10^7$ Da.

Modification of Polycationic Materials

Polyethylenimines are a subset of polycationic polymeric materials having the general structure:

(IX)

where n is 2 to 10, p is greater than 1, and R4 is independently in each instance one of a hydrogen atom, a linear segment (secondary amines), or a branched segment (at least one tertiary amine). Linear segments have the general structure:

(X)

where n is 2 to 10. Branched segments include at least one group having the general structure:

(XI)

where n is 2 to 10.

A linear segment corresponds to two or more repeating groups (X) directly connected to each other. A branched segment includes a repeating group (XI) connected to two other repeat units, either of which or both can be a (X) repeating group or a (XI) repeating group. The ratio of (X) repeating groups to (XI) repeating groups is not limited and all, or substantially all, repeating units may be (X) repeating groups. In the above structures (X) and (XI), s and r designate that the depicted groups are repeating units within a polymeric material and when given numerical values may correspond to statistical ratios (compositional percentages) within a given polymeric material or specific chain. For a linear or substantially linear polymeric material, the ratio of s to r would be zero or approximately zero. For a dendrimeric material, the ratio of r to s could be zero or approximately zero. The starred bonds on the amine ends of structures (X) and (XI) correspond to a primary amine end group (*—$(CH_2)_n$—$NH_3$), an alkyl end of another repeating unit (X)/(XI), or a connection point to other copolymer repeat units. The starred bonds on the alkyl ends of structures (X) and (XI) correspond to attachment points to the amine end of another repeating unit (X)/(XI), a primary amine end group (*—$NH_3$), or a connection point to other copolymer repeat units. In general, p in structure (IX) would be set such that the molecular weight (Mw) of the polymeric material would be in a range of 100 Da to $10^7$ Da. In some embodiments, n in structure (IX) would be between 2 and 5. In some embodiments, the weight-average molecular weight (Mw) of the polymeric material would be in a range of 10 kDa-50 kDa.

Polymeric materials corresponding to the structure (IX) can be modified by reaction (XII) with CPTE materials corresponding to the description of CPTE 120 above to give modified polycationic materials analogous to modified PEI 130.

(XII)

where m is from 2 to 10, n is from 2 to 4, p is greater than 1, R1 includes at least one carbon, and R4 is independently in each instance one of a hydrogen atom, a linear segment (secondary amines), or a branched segment (at least one tertiary amine), as described above. In some embodiments, R1 can include an alkyl group, an aryl group, a polymeric group, an oligomeric group, and/or a functional group permitting linkage to an alkyl group, an aryl group, a polymeric group, or an oligomeric group. In the above, in general, p would be set such that the resulting modified polycationic material would have weight-average molecular weight (Mw) greater than 100 Da and less than $10^7$ Da.

Gene Therapy Process

Figure 2:
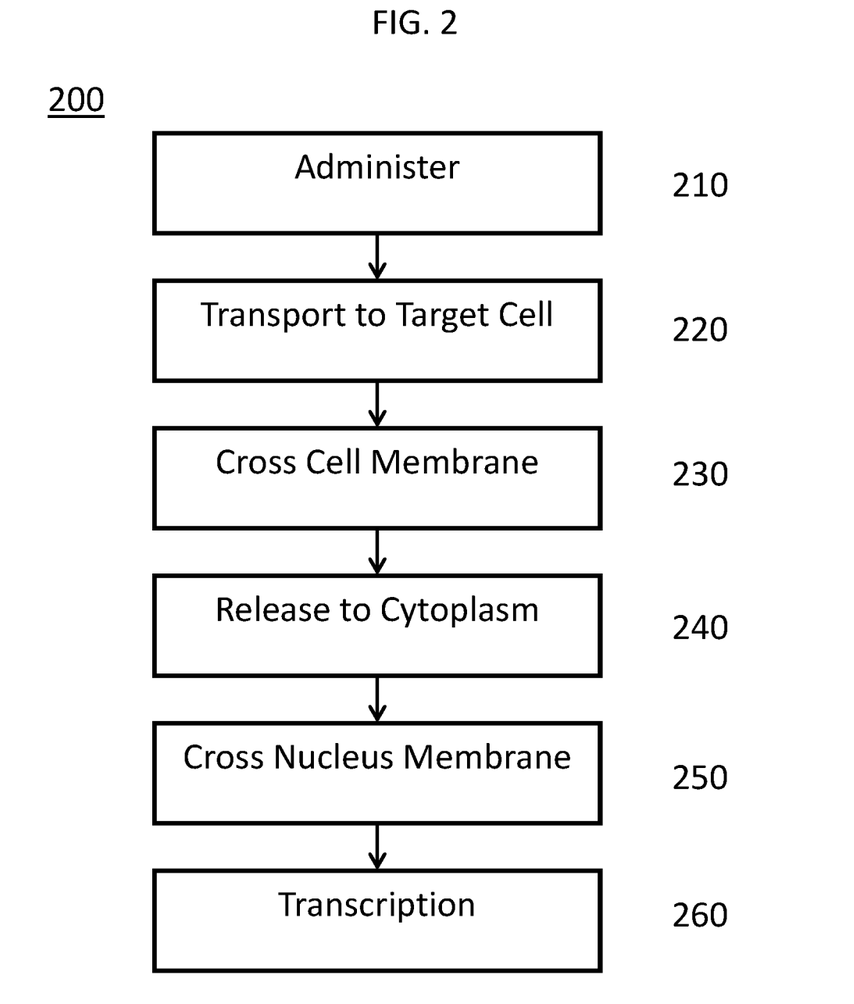
FIG. 2 depicts aspects of a gene therapy process.

FIG. 2 depicts aspects of a gene therapy process. The depicted process 200 assumes a genetic material has been identified as a possible therapeutic agent to be transfected into a cellular target of a specific type. The genetic material would typically be administered (element 210) to a patient by topical application, ingestion, injection, intravenous line, or the like. Here, the genetic material might also be administered to cells or tissues outside the body (in vitro administration) for research or therapeutic purposes. The therapeutic agent will typically be transported to the cellular target (element 220) by available transport pathways of the body (e.g., blood vessels, capillaries, lymphatic ducts, or the like for in vivo administration) or diffusion (for in vitro processes).

Bare, unprotected genetic material would be subject to enzymatic degradation, attack by the patient's immune system, and/or removal before reaching or entering the cellular target, therefore the therapeutic genetic material is typically incorporated with a "delivery vehicle" for administration and protection during transport to the target cell. Various classes of delivery vehicles include viruses, liposomes, and polymers.

Once at the target cell, the genetic material must cross the cell membrane (element 230). The delivery vehicle can increase the probability of the genetic material crossing the cell membrane by being designed to preferentially bind (or otherwise interact) with a target cell's outer membrane.

There are various mechanisms for genetic material to cross a cell membrane, but with polymeric delivery vehicles the entrance process generally proceeds by endocytosis, which results in the genetic material being, at least transiently, surrounded within an endosome inside the cell target. The effectiveness of the genetic material as a therapeutic agent is limited while it is trapped inside the endosome, therefore the genetic material is preferably released from the endosome into the cell target's cytoplasm (element 240).

Once released to the cytoplasm, the genetic material must ultimately cross the cell target's nuclear membrane (element 250) to be accessible for transcription (element 260) by the cell's own transcription machinery for gene expression.

As noted, polyethylenimines have been studied as polymeric delivery vehicles for gene therapy applications. In particular, 25 kDa high molecular weight polyethylenimine (PEI), which contains primary, secondary and tertiary amine groups, is known to provide high gene transfection efficiency for in vitro applications. Furthermore, polyethylenimine has a high cationic charge density at physiological pH levels, such that about 20% of amine groups (i.e., primary amines) are protonated. This allows polyethylenimine to form electrostatic interactions with negatively charged nucleic acids (genetic material components) over a relatively broad pH range and to complex genetic material into polyplexes (which may be considered nanoparticles or nanocomplexes). Once polyethylenimine/nucleic acid nanocomplexes are internalized into the cells, the secondary and tertiary amines facilitate the release of the genetic material from the endosomes through the "proton sponge effect." Furthermore, once released from the endosome, the complexed genetic material can "decomplex" and become available for diffusion/transport across the nucleus membrane (and eventual transcription).

Various polyethylenimine and polyethylenimine derivatives have been successfully used for in vivo gene transfer of therapeutic DNA molecules and siRNAs. However, despite high gene transfection efficiency, polyethylenimine materials have problems with toxicity, aggregation, and undesired non-specific interactions with cellular and non-cellular components, resulting in adverse effects particularly for in vivo administration.

To reduce or eliminate the potential adverse effects, various modifications of polyethylenimine molecules have been previously explored. Modifications include grafting polyethylenimines with saccharides such as oligo-maltose, poly(ethylene glycol), chitosan, and oligosaccharides (such as galactose and mannose). In general, these previous modifications have been insufficient with respect to reducing in cytotoxicity and other adverse effects (e.g., agglomeration) without also undesirably reducing transfection efficiency.

However, modified polycationic polymers, such as modified PEI 130 described above, are zwitterionic polymers (or include zwitterionic moieties) that are similar to polyethylene glycol (PEG)-based materials in that they will be highly hydrophilic. As highly hydrophilic polymers (or polymers with highly hydrophilic moieties), these modified polymers can be surrounded by a hydration layer when in aqueous media. Generating a hydration layer in this fashion is considered one of the key means for providing "stealth" properties in biomaterials. As noted, "stealth" refers to the ability of a material to resist cell adhesion, antibody opsonization, and non-specific protein interactions, which minimizes detection and clearance of these materials by the patient's immune system. Thus, the modified polycationic polymers of the present disclosure (e.g., modified PEI 130) will tend to have stealth characteristics, while still maintaining polycationic aspects of "unmodified" polycationic polymers that allow the complexing of genetic material (formation of polyplexes) and attractive electrostatic interactions with cellular membranes. Furthermore, the modified polycationic polymers can still include moieties favorable for the promotion of endosomal release via the proto sponge effect such as found in "unmodified" polyethylenimines. Additionally, modified polycationic polymers (e.g., modified PEI 130) of the present disclosure are potentially biomimetic since they share structural similarities with the phosphatidylcholine-based moieties of biological membranes.

Figure 3:
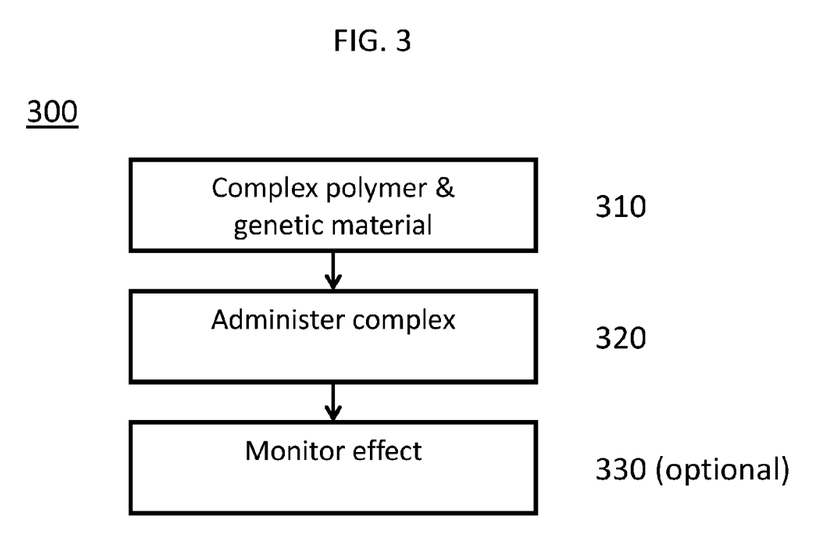
FIG. 3 depicts aspects a gene therapy process in which a modified polycationic polymeric material according to an embodiment can be used.

FIG. 3 depicts aspects of a gene therapy method using a modified polyethylenimine. In gene therapy method 300, a modified polycationic polymer (such as modified PEI 130 described above) is brought into contact with genetic material and the modified polycationic polymer and the genetic material form a complex (element 310). The genetic material may be DNA, RNA, or another material comprising nucleic acids. The manner of bringing the modified polycationic polymer and the genetic material into contact is not limited. In general, any contacting between the materials that allows the formation the necessary complex is acceptable. The complex is then administered (element 320). The complex may be administered to cellular targets in vivo or in vitro. Administration methods are not particularly limited and may include, without limitation, topical application, ingestion, injection, intravenous line, or the like. The effect of the administered complex may be optionally monitored (element 330). Monitoring of the effect may include, without limitation, evaluation of overall patient health, detection/measurement of specific protein levels, evaluation of cellular viability, and the like.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A polymeric material, comprising:
a polyethylenimine-based component having a structure:

and including a group attached thereto at the starred bond location having the general structure:

wherein
each instance of R2 is independently one of a hydrogen atom, a linear polyethylenimine segment, a branched polyethylenimine segment, a copolymeric segment including a linear polyethylenimine segment, or a copolymeric segment including a branched polyethylenimine segment,
m is greater than two,
R1 includes a carbon atom, and
n is from 2 to 4.

2. The polymeric material according to claim 1, wherein n is equal to 2.

3. The polymeric material according to claim 1, wherein n is equal to 3.

4. The polymeric material according to claim 1, wherein n is equal to 4.

5. The polymeric material according to claim 1, wherein R1 is an alkyl group.

6. The polymeric material according to claim 5, wherein R1 is a methyl group.

7. The polymeric material according to claim 1, wherein R1 is a polymeric group.

8. The polymeric material according to claim 1, wherein R1 comprises a linkage to a poly(ethylene glycol).

9. The polymeric material according to claim 1, wherein the polyethylenimine-based component is linear.

10. The polymeric material according to claim 1, wherein the polyethylenimine-based component is branched.

11. The polymeric material according to claim 1, wherein polyethylenimine-based component is dendrimeric.

12. The polymeric material according to claim 1, wherein the polyethylenimine-based component is branched, n is equal to 2, R1 is methyl, and the polymeric material has a weight-average molecular weight (Mw) of between 10 kDA to 50 kDa.

13. The polymeric material according to claim 1, wherein the polyethylenimine-based component is in a complex with a genetic material.

14. A method of making a polymeric material, comprising:
contacting a polyethylenimine-based material having the general structure with a cyclic phosphotriester having the general structure wherein
R1 includes a carbon atom,
n is from 2 to 4,
each instance of R2 is independently one of a hydrogen atom, a linear polyethylenimine segment, or a branched polyethylenimine segment, and
m is such that a weight-average molecular weight (Mw) of the polyethylenimine-based material is between 100 Da to $10^7$ Da.

15. The method of claim 14, wherein n is equal to 2.

16. The method of claim 14, wherein R1 is a methyl group or an ethyl group.

17. The method of claim 14, wherein the polyethylenimine-based material is dissolved in a solvent.

18. The method of claim 14, wherein at least one instance of R2 is a branched polyethylenimine segment.

19. A method for forming polymeric delivery vehicles for transfecting a target body with genetic material, comprising:
complexing a genetic material and a polymeric material including a polyethylenimine-based component having the structure:

and having a group attached thereto at the starred bond with a structure corresponding to the following:

wherein
each instance of R2 is independently one of a hydrogen atom, a linear polyethylenimine segment, a branched polyethylenimine segment, a branched polyethylenimine segment, a coplymeric segment including a linear polyethylenimine segment, or a copolymeric segment including a branched polyethylenimine segment,
m is greater than two,
R1 includes a carbon atom, and
n is from 2 to 4.

20. The method of claim 19, further comprising:
administering the genetic material to a target body while the genetic material is complexed with the polymeric material.

* * * * *